United States Patent [19]

Cielo et al.

[11] Patent Number: 4,659,937
[45] Date of Patent: Apr. 21, 1987

[54] OPTICAL DEVICE FOR MEASURING THE DIAMETER AND DETECTING SURFACE DEFECTS OF MOVING WIRE

[75] Inventors: Paolo Cielo, Montreal; Ghislain Vaudreuil, Boucherville, both of Canada

[73] Assignee: Canadian Patents and Development Limited, Ottawa, Canada

[21] Appl. No.: 797,048

[22] Filed: Nov. 12, 1985

[51] Int. Cl.⁴ .................. G01N 21/86; G01N 21/88
[52] U.S. Cl. ............................. 250/560; 250/572; 356/430
[58] Field of Search ............ 250/560, 562, 571, 572; 356/384, 385, 430

[56] References Cited

U.S. PATENT DOCUMENTS

| | | | |
|---|---|---|---|
| 3,804,529 | 4/1974 | Hausler | 250/571 X |
| 3,901,606 | 8/1975 | Watanabe et al. | 250/560 X |
| 4,007,992 | 2/1977 | Petrohilos et al. | 250/571 X |
| 4,019,066 | 4/1977 | Lucas et al. | 250/562 |
| 4,061,427 | 12/1977 | Fletcher et al. | 356/384 |
| 4,166,214 | 8/1979 | Fuchs-Viniczay et al. | 250/227 |
| 4,269,514 | 5/1981 | Vossberg | 250/560 X |
| 4,441,817 | 4/1984 | Pryor | 356/384 X |
| 4,493,554 | 1/1985 | Pryor et al. | 250/562 X |
| 4,515,479 | 5/1985 | Pryor | 356/384 X |

Primary Examiner—Eugene R. LaRoche
Assistant Examiner—David Mis
Attorney, Agent, or Firm—Yoshiharu Toyooka

[57] ABSTRACT

An apparatus using optical techniques for simultaneously detecting surface defects and measuring the diameter of a wire coming out from an extruder. A combination of cylindrical lenses is used for projecting, perpendicularly across the longitudinal axis of the wire, a sharply focused laminar beam. This apparatus includes an optical source system for emitting optical rays, an optical system for focusing the rays on the wire, an optical detector system for receiving the rays and generating a detector signal to be processed by a signal processing system, the processing system generates an electric signal indicative of the amplitude of the defects and another electric signal indicative of the diameter of the wire.

16 Claims, 12 Drawing Figures

OPTICAL DEVICE FOR MEASURING THE DIAMETER AND DETECTING SURFACE DEFECTS OF MOVING WIRE

FIELD OF THE INVENTION

This invention relates to an automatic inspection system for moving wires. It is a non-contact type apparatus for simultaneously detecting the magnitude of defects distributed over the surface of the wire and measuring the diameter of the wire. The apparatus makes a real time inspection of the wire and it can be used at high wire temperatures. Plastic-coated wires are extruded at speed of 10 to 20 m/sec through a die in a plastic-melting cell. Surface defects such as blisters produced by the infiltration of gas, moisture in the cell, unfused pellets caused by insufficient extruder temperature, inadequate pressure in the cell or other defects are unacceptable to the customers. Typical amplitudes of the defects to be detected are in the 50 μm range and spatial periods of the defects over the surface of the wire are typically 500 μm.

DESCRIPTION OF THE PRIOR ART

Optical techniques are a good choice for such an application because they are non-contact and fast; they have a high degree of resolution and they can detect exactly the kind of defects which can be visually detected by the customer. There have been a number of devices constructed or proposed for optically measuring the dimensions of an object. Some of these devices use a scanning light beam projector, some others use a scanning light detector and still others use a stationary beam technique.

Known in the art is an apparatus for measuring the diameter of an elongated member (U.S. Pat. No. 3,765,774, Oct. 16, 1973 Petrohilos). The apparatus uses a scanning light beam method where a light beam is scanned across the wire. Rotating mirrors receive a narrow laser beam from a light source and project a rotary scanning beam to a lens which converts it into a parallel scanning beam. An article to be measured is positioned in the path of the parallel scanning beam and the interruptions of the beam, as produced by the article, are sensed by a photodetector.

Also known in the art is a non-contact type dimension measuring device (U.S. Pat. No. 3,901,606 Aug. 26, 1975 Watanabe et al). The apparatus uses the scanning light detector method where collimated rays are projected across the object to be measured. A convex lens, situated on the opposite side of the object, receives the collimated rays and projects them on an array of photodetectors. The photodetectors are electronically scanned in order to detect the projected shadow of the object.

Also known in the art is an opto-electrical system for monitoring filaments of fine configuration (U.S. Pat. No. 4,166,214 Aug. 28, 1979 Fuchs-Vinizay et al). The system uses a stationary beam technique where a light beam is projected across the filament and is received by a light guide situated on the opposite side of the filament. The light guide is coupled to a photodetector.

Although all the above systems are suitable for measuring the diameter of the wire, none of these systems can detect the surface defects mentioned above without problems. The apparatus disclosed in the U.S. Pat. Nos. 3,765,774 and 3,901,606 don't have the measuring scanning speed for the detection of the defects at extrusion speeds of more than 10 m/sec. The apparatus disclosed in U.S. Pat. No. 4,166,214 uses the schlieren technique which limits its use to small objects such as fibers, it is also very delicate to align and it requires expensive optical instrumentation.

There are needs for a non-contact type apparatus for simultaneously detecting the magnitude of the defects and measuring the diameter of the wire rapidly and with a high degree of sensibility.

Another need is to achieve the above measurement by a simple and inexpensive technique.

SUMMARY OF THE INVENTION

According to the present invention there is provided a non-contact type apparatus for simultaneously detecting surface defects and measuring the diameter of an elongated object moving along its longitudinal axis comprising:

- an incoherent optical source system for emitting incoherent optical rays;
- an optical system situated between the optical source system and the object for focusing the optical rays to form a substantially converging uniform laminar beam lying in a plane substantially perpendicular to the longitudinal axis of the object and for projecting the said laminar beam toward the said object; and
- an optical detector system aligned with the optical system on the opposite side of the object for receiving the optical rays to generate a detector signal indicative of surface defects and the diameter of the object.

BRIEF DESCRIPTION OF THE DRAWINGS

The accompanying drawings illustrate, by way of example, embodiments of the present invention, in which.

DETAIL DESCRIPTION OF THE PREFERRED EMBODIMENT

Figure 1:
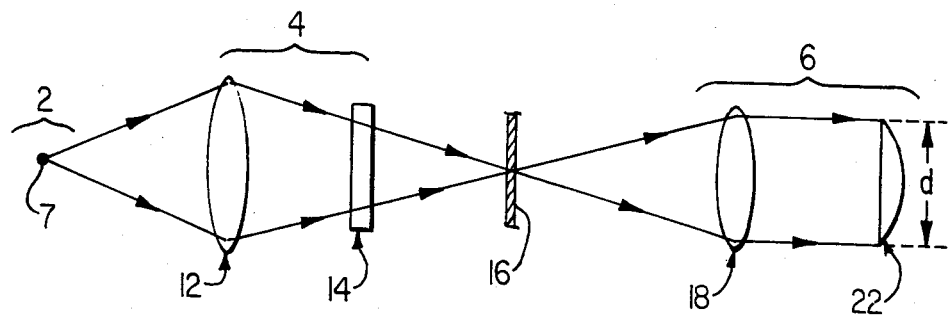
FIG. 1 is a top view of a non-contact type apparatus for simultaneously detecting surface defects and measuring the diameter of an elongated object, according to one embodiment of the present invention.
Figure 2:
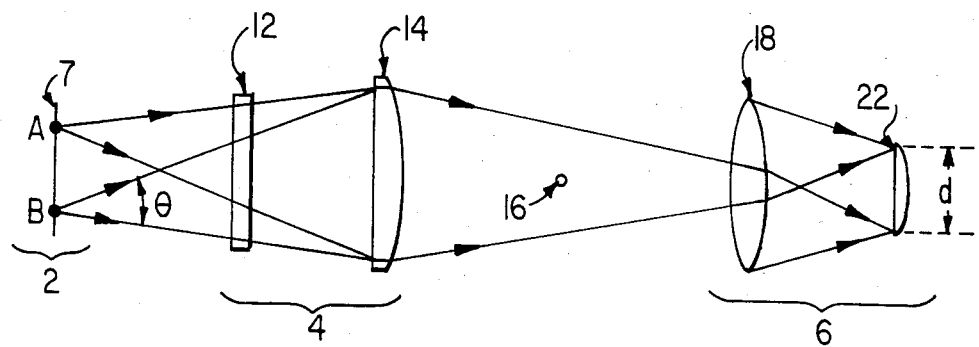
FIG. 2 is a side view of the apparatus shown in FIG. 1.

In FIG. 1 and in FIG. 2, there is shown a non-contact type apparatus for simultaneously detecting surface defects and measuring the diameter of an elongated object moving along its longitudinal axis comprising:

an optical source system 2 for emitting optical rays;

an optical system 4 situated between the optical source system 2 and the object 16 for focusing the optical rays as a laminar beam substantially perpendicular to the longitudinal axis of the object 16; and an optical detector system 6 aligned with the optical system 4 on the opposite side of the object 16 for receiving the optical rays and to generate a detector signal indicative of surface defects and the diameter of the object 16.

The optical source system 2 includes a linear filament lamp 7 oriented with its longitudinal axis perpendicular to the longitudinal axis of the object 16. The filament lamp 7 emits optical rays in the visible range so that the alignment of the optical rays toward the object 16 can be done easily. The filament lamp 7 produces optical rays of short coherent length which eliminates speckle problems observed with a source of coherent light. These speckle problems are produced by the presence of dust or grease particles on optical windows and lenses. The optical system 4 includes a first cylindrical lens 12 and a second cylindrical lens 14, which is preferably a plano-convex one, for projecting the image of the filament in the form of a laminar beam perpendicular to the longitudinal axis of the object 16. The first cylindrical lens 12 is oriented with its longitudinal axis parallel to the filament lamp 7 and perpendicular to the longitudinal axis of the object 16 while the second cylindrical lens 14 is oriented perpendicularly to the first lens 12. The portion of the laminar beam that is not blocked by the object 16 is collected by the optical detector system 6.

The first cylindrical lens 12 is used to converge the optical rays to focus the image of the filament lamp 7 on the elongated object 16 and the second cylindrical lens 14 is used for projecting a collimated beam in a plane perpendicular to the axis of the elongated object 16. The combined action of the two cylindrical lenses produces a collimated beam line perpendicular to the longitudinal axis of the object 16. The optical detector system 6 includes a spherical lens 18 and a single silicon detector 22. The spherical lens 18 receives the optical rays which have passed across the object 16; the action of this lens 18 is double, first it collimates the rays in a first plane which is parallel to the longitudinal axis of the object 16 and second it focuses the rays in a second plane perpendicular to the first plane. The single silicon detector 22 receives the rays which are unobstructed by the object 16 and generates a detector signal, the DC component of the detector signal depends on the diameter of the object 16 along the projected laminar beam. Sudden variations of the detector signal, produced by the presence of surface defects on the moving object 16, produce an AC signal component proportional to the amplitude of the surface defects independently of the object 16 position or vibration.

The portion AB of the filament lamp 7 is diaphragmed by the aperture of the detector through the second cylindrical lens 14 and the spherical lens 18 having focal lengths $F_1$ and $F_2$ respectively.

Figure 4:
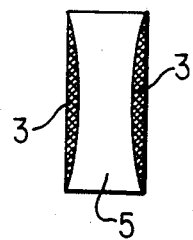
FIG. 4 is a front view of the second cylindrical lens of the apparatus shown in FIG. 1.

The relation $$AB = \left(\frac{F_2}{F_1}\right) d,$$

where d is the aperture diameter of the detector, holds between such parameters. All the portion of the filament lamp 7 between the points A and B contribute to the illumination of each portion of the projected laminar beam on the object 16, so that eventual hot or cold spots along the filament lamp 7 are averaged out. The lateral oscillation of the object 16 will affect the signal only if the angular distribution $\theta$ of the lamp emission across the aperture of the second cylindrical lens 14 is non-uniform. If this is the case, the second cylindrical lens 14 may be conveniently masked as shown in the FIG. 4 where the shadowed areas 3 represent the masked portions and the white area 5 represents the transparent portion of the lens. The gradual accumulation of specks or molten plastic droplets on the second cylindrical lenses 14, on the spherical lens 18 or on any window situated in the beam path will hardly affect the level of the detector signal as a function of the elongated object transverse position because of the averaging action along the focussed laminar beam. A decrease in the DC signal level produced by excessive dirt accumulation or by light intensity fading because of lamp aging would trigger an alarm requesting maintenance.

The amplitude of the AC component of the detector signal fluctuates in the presence of the surface defects at a frequency F of the order of $$F = v/p \tag{1}$$

where $v$ is the speed of the object 16, typically between 10 m/s and 20 m/s, and p is the spatial period of the surface defects typically 500 μm.

In order to properly detect the defects, the width w of the laminar beam intersecting the object 16 should be smaller than p.

Such a width is in this case:

$$w = M \times D \tag{2}$$

where M is the magnification of the first cylindrical lens 12 and D is the width of the filament lamp 7:

The magnitude M is $$M = S_i/S_o \tag{3}$$

where $S_i$ is the distance between the focused image of the filament lamp 7 and the first cylindrical lens 12 and $S_o$ is the distance between the filament lamp 7 and the first cylindrical lens 12.

The equation (2) provides a cutoff frequency $F_c$ $$F_c = v/w \tag{4}$$

above which the detector signal is rapidly attenuated.

Figure 3:
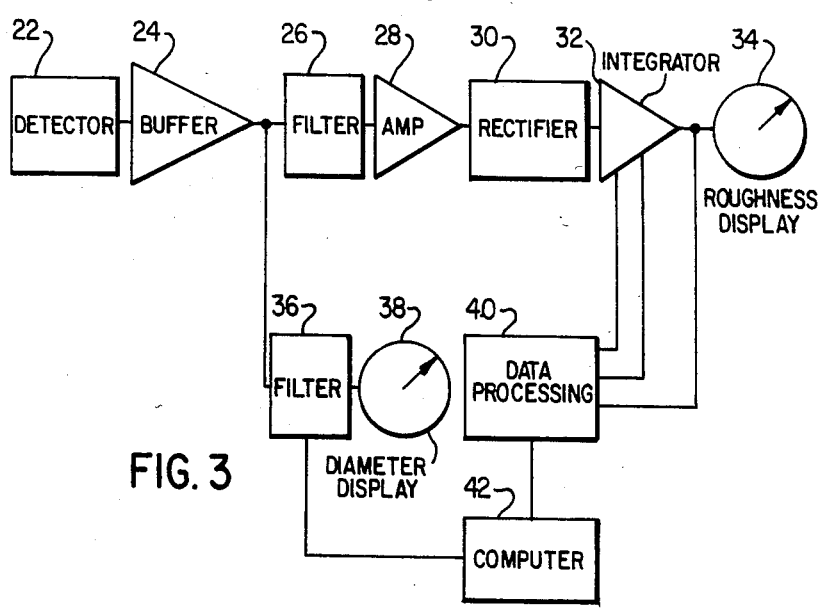
FIG. 3 is a schematic diagram in block form of signal processing electronics for processing the detector signal generated by the apparatus shown in FIG. 1.

Referring now to FIG. 3, there is shown a signal processing system for establishing simultaneously the magnitude of the surface defects and the diameter of the object 16. The single silicon detector 22 sends the detector signal to a band-pass filter 26 via a buffer 24 and to a low-pass filter 36 via the same buffer 24. The band-pass filter 26 should be centered around the frequency given by equation 1 which is based on the spatial period of surface defects to be detected. The output of the band-pass filter 26 is an AC signal relating to the magnitude of the surface defects. The AC signal is fed to an amplifier 28, rectified by a rectifier 30 and then integrated by a gated integrator 32 to avoid isolated transient which may be produced by ambient noise. The output of the gated integrator 32 is fed to a first meter 34 for displaying the magnitude of the detected surface defects. The lower frequency limit of the band-pass filter must be determined to avoid low frequency noise due to irregular intensity along the focused beam line. The output of the low-pass filter 36, a DC signal, is fed to a second meter 38 for displaying the diameter of the object 16. The low-pass filter 36 is monitored by a computer 42 which supplies a proper reference signal. Periodical calibration could be performed on the reference signal to avoid absolute signal variations caused by aging of the optical source system and the optical detector system 6, or dirt deposit on the lens surfaces. Such an operation would be performed very quickly, the operator having to reset the system with a standard diameter elongated object held in front of the optical detector system 6. The gated integrator 32 is also monitored by the computer 42 via a logic circuit 40.

Figure 5:
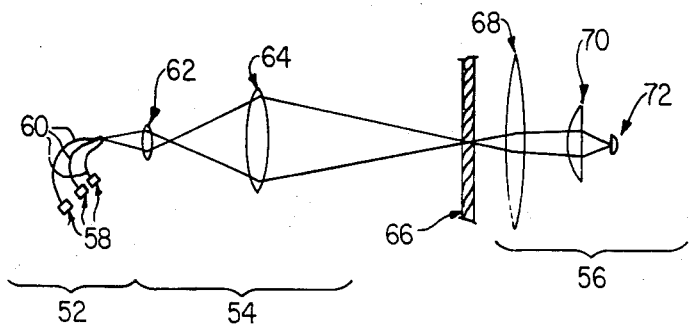
FIG. 5 is the top view of another embodiment of the non-contact type apparatus for simultaneously detecting surface defects and measuring the diameter of an elongated object.
Figure 6:
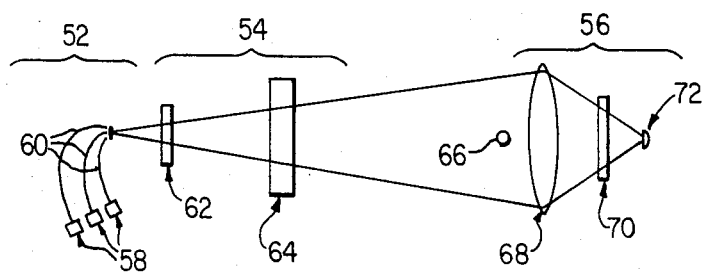
FIG. 6 is the side view of the apparatus shown in FIG. 5.

Referring now to FIG. 5 and FIG. 6, there is shown another embodiment of the non-contact type apparatus for simultaneously detecting surface defects and measuring the diameter of an elongated object. The apparatus shown in FIG. 5 and FIG. 6 comprises an optical source system 52, an optical system 54 and an optical detector system 56. The optical source system 52 includes three multimode diode lasers 58, each diode is individually coupled to a multimode optical fiber 60. The diode lasers 58 emit a near infrared beam of 2 mW, the typical wavelength of the infrared beam is 830 nm. The use of multimode diode lasers 58 with multimode optical fibers 60 produce optical rays, emerging from the fiber ends after multiple internal reflections within the fiber, that are no longer coherent. A multimode optical fiber having a length of 1 meter would produce enough internal reflections to generate incoherent optical rays. The incoherent optical rays eliminate interference effect produced by dust or grease particles on lenses.

The optical system 54 includes a first cylindrical lens 62 and a second cylindrical lens 64 for projecting a focused laser line perpendicular to the longitudinal axis of the object 66. The first and second cylindrical lenses have their longitudinal axis perpendicular to the longitudinal axis of the object 66. The first cylindrical lens 62 focuses the rays of the optical source 52 as a sharp laser line which is the image of the source as projected by the first cylindrical lens 62, the second cylindrical lens 64 projects the image of the first lens 62 on the object 66 as a sharp laser line which is substantially perpendicular to the longitudinal axis of the object 66. The portion of the laser line that is not blocked by the object 66 is collected by the optical detector system 56.

The optical detector system 56 includes a spherical lens 68, a third cylindrical lens 70, which is preferably a plano-convex one, and a single silicon detector 72. The spherical lens 68 receives the optical rays which have passed across the object 66 and directs the rays on the third lens 70. The action of the spherical lens is double, first it collimates the rays in a first plane which is parallel to the longitudinal axis of the object, and second it focuses the rays in a second plane which is perpendicular to the first plane. The third cylindrical lens 70 focuses the rays in the first plane on the single silicon detector 72. The silicon detector 72 generates a detector signal responsive to the magnitude of the defects distributed over the object circumference and also responsive to the diameter of the object 66. If the intensity along the focused laser line is constant, a short range excursion of the object laterally such as the vibration of the object 66 coming out of an extruder, do not affect the detector signal.

In order to properly detect the defects, the width w of the laser line intersecting the object 66 should be smaller than p, the spacial period of surface defects. Such a width is in this case:

$$w = \frac{i_1 i_2 d}{\sigma_1 \sigma_2} \tag{5}$$

where $\sigma_1$ is the distance between the output ends of the optical fibers 60 and the first cylindrical lens 62, $\sigma_2$ is the distance between the image of the first lens 62 and the second lends 64, $i_1$ is the distance between the first lens 62 and the image of the first lens 62, $i_2$ is the distance between the second lens 64 and the object 66 and d is the diameter of the optical fibers 60, typically 50 μm.

The first cylindrical lens is not absolutely necessary because one lens is sufficient for focusing the laser beam as a sharp laser line. However if $\sigma_1 > i_1$ it may help lowering w, as shown in equation 5, making it possible to increase the ratio $i_2/\sigma_2$ and thus the field's depth of the projected laser line. This is possible at the expense of a loer intensity of the laser line.

Figure 7:
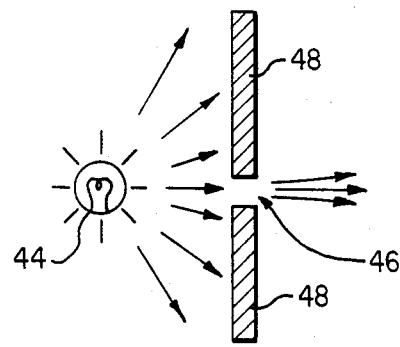
FIG. 7 is an alternative embodiment of the optical source system of the apparatus shown in FIG. 5.

Referring now to FIG. 7, there is shown an alternative embodiment of the optical source system for producing incoherent optical rays. The alternative embodiment includes an incoherent light source such as a lamp 44 followed by an opaque member 48 having a slit 46 oriented toward the optical system 4 whereby optical rays are projected toward the object 16. The available light intensity would be much smaller in this case.

EXPERIMENTAL RESULTS

Figure 8:
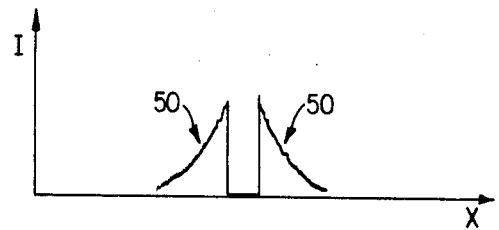
FIG. 8 is a typical profile of light intensity, obtained with a single source of highly coherent laser beam, along the beam line after projection through the object.
Figure 9:
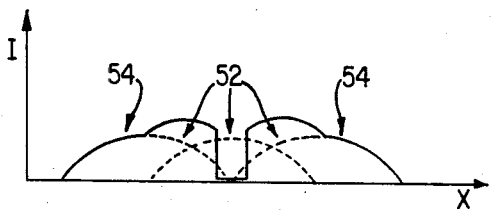
FIG. 9 is a typical profile of light intensity, obtained with three multimode diode lasers, along the beam line after projection through the object.

In FIG. 8 and FIG. 9, there are shown graphs where the vertical axis repesents light intensity and the horizontal axis represents distance along the width of the laminar beam after projection through the object.

A problem was observed when generating a line using a single laser source as a He-Ne laser. In theory, the line intensity shown in FIG. 8 should be perfectly smooth. In practice, the presence of minute dust particles or fingerprints in the lenses or windows, which are unavoidable in the real environment, produces considerable speckle noise, visible as closely-spaced irregularities along the curve of the kind shown in FIG. 8. Such a noise is produced by the interference of the highly coherent laser beam randomly scattered by the dust or grease particles. Such line irregularities as seen on FIG. 8 are low in amplitude but high in spatial frequency, so that they strongly affect the local value of the curve slope near the two cutoff points. This results in important AC signal fluctuations when the wire vibrates with a low amplitude but at high frequency.

The line obtained with the array of the laser-diodes, FIG. 9, is much less affected by such fluctuations. The dot line represents the individual laser light intensity and the continuous line represents the cumulative light intensity. The reason for this is that the diodes are multimode and are transmitted through a length of the order of 1 m of multimode fibers, so that multiple reflections within the fibers completely destroy the initial coherence of the laser beam. Speckle effects are thus no longer present, and the projected line is much smoother.

Figure 10:
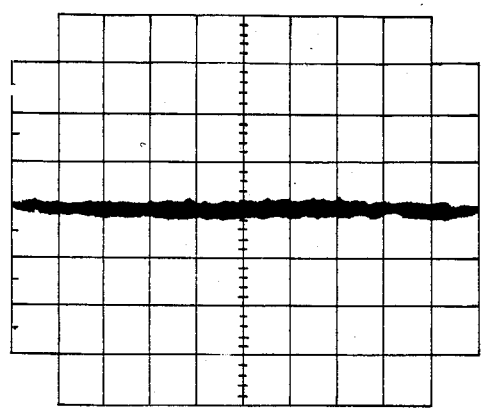
FIG. 10 is a waveform diagram showing, by way of example, AC signal generated by the apparatus shown in FIG. 1 and FIG. 2 with motionless wire.

The apparatus shown in FIG. 1 and FIG. 2 was experimented. The roughness-monitoring prototype was set with XLPE wire. On FIGS. 10, 11 and 12, the vertical axis represents the magnitude of the detected AC signal and the horizontal axis represents the time, one horizontal division corresponds to 5 ms on FIG. 10 and 50 ms on FIGS. 11 and 12. FIG. 10 shows the AC signal obtained with a motionless wire, one vertical division corresponds to 15 $\mu$m. The amplitude of such a signal represents the intrinsic noise intensity generated by the apparatus, such noise is equivalent to a wire-diameter variation of approximately 5 $\mu$m.

Figure 11:
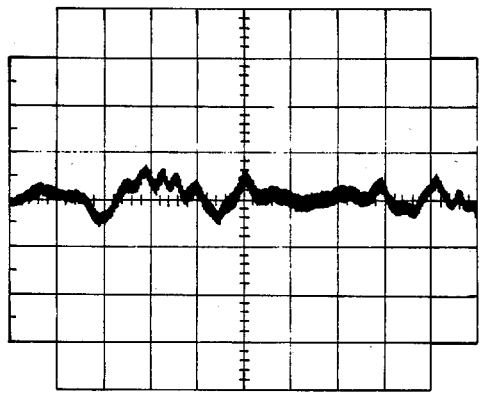
FIG. 11 is a waveform diagram showing, by way of example, AC signal generated by the apparatus shown in FIG. 1 and FIG. 2 with wire of acceptable surface quality.

FIG. 11 shows the AC signal obtained with a wire of acceptable surface roughness sliding at 0.1 m/s. One vertical division corresponds approximately to 15 $\mu$m.

Figure 12:
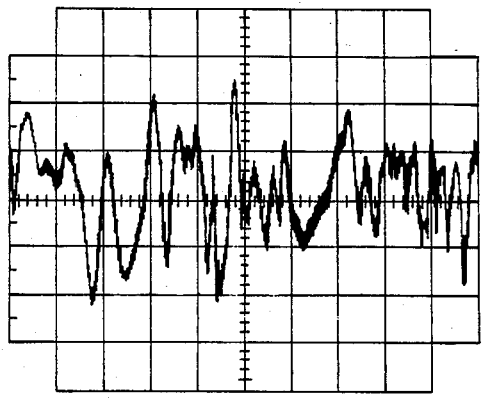
FIG. 12 is a waveform diagram showing, by way of example, AC signal generated by the apparatus shown in FIG. 1 and FIG. 2 with wire of unacceptable quality.

FIG. 12 shows the AC signal obtained with a wire of unacceptable surface roughness sliding at 0.1 m/s. One vertical division corresponds approximately to 60 $\mu$m.

We claim:

1. A non-contact type apparatus for simultaneously detecting surface defects and measuring the diameter of an elongated object moving along its longitudinal axis comprising:
   an incoherent optical source system for emitting incoherent optical rays;
   an optical system situated between the optical source system and the object for focusing the optical rays to form a substantially converging uniform laminar beam lying in a plane substantially perpendicular to the longitudinal axis of the object and for projecting the said laminar beam toward the said object; and
   an optical detector system aligned with the optical system on the opposite side of the object for receiving the optical rays to generate a detector signal indicative of the surface defects and the diameter of the object.

2. The apparatus as defined in claim 1 wherein the incoherent optical source comprises a linear filament lamp.

3. The apparatus as defined in claim 1 wherein the incoherent optical source comprises at least one multimode diode laser and one multimode optical fiber where each optical fiber is individually coupled to each diode laser at one end of the fiber and aligned in a plane perpendicular to the longitudinal axis of the object at the other end.

4. The apparatus as defined in claim 3 wherein the incoherent optical source comprises three multimode diode lasers and three multimode optical fibers.

5. The apparatus as defined in claim 2 wherein the optical system comprises:
   a first cylindrical lens being situated between the optical source system and the object for focusing the image of the lamp on the object, the first cylindrical lens being oriented with its longitudinal axis parallel to the longitudinal axis of the lamp filament; and
   a second cylindrical lens being situated between the optical source system and the object for collimating the rays and oriented perpendicularly to the first cylindrical lens.

6. The apparatus as defined in claim 3 wherein the optical system comprises a cylindrical lens being situated between the optical source system and the object, for projecting said laminar beam substantially perpendicularly to the longitudinal axis of the object.

7. The apparatus as defined in claim 3 wherein the optical system comprises:
   a first cylindrical lens for focusing the optical rays coming from the optical source system, the first cylindrical lens being oriented with its longitudinal axis perpendicular to the longitudinal axis of the object; and
   a second cylindrical lens being situated between the first cylindrical lens and the object, for focusing the image of the first lens on the object.

8. The apparatus as defined in claim 2 wherein the optical detector system comprises:
   a spherical lens being aligned with the optical system on the opposite side of the object for simultaneously collimating the rays in the first plane which contains the center of the lens and the longitudinal axis of the object and focusing the rays in a second plane which is perpendicular to the longitudinal axis of the object; and
   an opto-electrical detector being aligned with the rays for generating a detector signal responsive of the surface defects and the diameter of the object.

9. The apparatus as defined in claim 3 wherein the optical detector system comprises:
   a spherical lens being aligned with the optical system on the opposite side of the object, for simultaneously collimating the rays in a first plane which contains the center of the lens and the longitudinal axis of the object and focusing the rays in a second plane which is perpendicular to the longitudinal of the object;
   a third cylindrical lens being aligned with the rays for focusing the collimated rays in the first plane; and
   an opto-electrical detector being aligned with rays for generating a detector signal responsive of the surface defects and the diameter of the object.

10. The apparatus as defined in claim 5 wherein the said second cylindrical lens has masked areas.

11. The apparatus as defined in claim 1 further comprising a signal processing system having:
   a band-pass filter connected to the buffer for extracting the AC component signal from the detector signal, the band-pass filter is centered around the frequency F according to the following equation:

$F = v/p$ where $v$ is the speed of the object and p is the spatial period of the surface defects;
   a first display means system connected to the band-pass filter for displaying the amplitude of the surface defects;
   a low-pass filter connected to the buffer for extracting the DC component from the detector signal;
   a second display means system connected to the low-pass filter for displaying the diameter of the object; and a computer means connected to the first and second display means systems for providing to each display means system a proper reference signal.

12. A method for simultaneously detecting surface defects and measuring the diameter of an elongated object moving alongs its longitudinal axis comprising steps of:
 (i) emitting incoherent optical rays from light source means;
 (ii) focusing the optical rays to form a substantially converging uniform laminar beam lying in a plane substantially perpendicular to the longitudinal axis of the object and for projecting the said laminar beam toward the said object;
 (iii) directing a portion of the optical rays, which has not been clocked by the object, toward an opto-electrical detector;
 (iv) generating an electric signal, by the detector, which is indicative of the surface defects and the diameter of the object.

13. The method as defined in claim 12 wherein the light source means is a linear filament lamp and the step (ii) of projecting the optical rays comprises steps of
 (v) focusing the image of the lamp on the object by means of a first cylindrical lens which is oriented with its longitudinal axis parallel to the longitudinal axis of the lamp filament;
 (vi) collimating the rays from the lamp by means of a second cylindrical lens which is oriented perpendicularly to the first cylindrical lens.

14. The method as defined in claim 12 wherein the light sorce means is a linear filament lamp and the steps (iii) of directing the rays comprises steps of:
 (vii) collimating the rays in a first plane which is parallel to the longitudinal axis of the object and contains the center of the detector;
 (viii) focusing the rays in a second plane which is perpendicular to the longitudinal axis of the object.

15. The method as defined in claim 12 further comprising steps of:
 (a) filtering the electric signal, for extracting an AC component signal with a band-pass filter centered around the frequency F according to the following equation:

$$F = v/p$$

where $v$ is the speed of the object and p is the spacial period of the surface defects, the AC component signal being responsive to the magnitude of the surface defects; and
 (b) low-pass filtering the electric signal, for extracting a first DC signal being indicative of the diameter of the object.

16. The method as defined in claim 15 further comprising steps of
 (a) converting the AC component signal to a second DC signal;
 (b) comparing the second DC signal with a first reference signal provided by a computer means for displaying the amplitude of the surface defects;
 (c) comparing the first DC signal with a second reference signal provided by the computer means for displaying the diameter of the object.

* * * * *